United States Patent [19]

Kramer et al.

[11] 4,123,805
[45] Nov. 7, 1978

[54] ARTIFICIAL HEART VALVE

[75] Inventors: Carl Kramer, Aachen; Hans J. Gerhardt, Cologne, both of Germany

[73] Assignee: Bayer Aktiengesellschaft, Leverkusen, Germany

[21] Appl. No.: 775,350

[22] Filed: Mar. 7, 1977

[30] Foreign Application Priority Data

Mar. 25, 1976 [DE] Fed. Rep. of Germany ....... 2612810

[51] Int. Cl.² .............................................. A61F 1/22
[52] U.S. Cl. ...................................... 3/1.5; 137/527.8
[58] Field of Search ............... 3/1.5, 1; 137/527, 527.8

[56] References Cited

U.S. PATENT DOCUMENTS

| 3,448,465 | 6/1969 | Pierce et al. | 3/1.5 |
| 3,476,143 | 11/1969 | Kaster | 3/1.5 X |
| 3,546,711 | 12/1970 | Bokros | 3/1.5 |
| 3,824,629 | 7/1974 | Shiley | 3/1.5 |
| 3,926,215 | 12/1975 | Macleod | 3/1.5 X |
| 4,011,601 | 3/1977 | Clune et al. | 3/1.5 |

FOREIGN PATENT DOCUMENTS 1,327,371  8/1973  United Kingdom .......... 3/1.5

Primary Examiner—Ronald L. Frinks
Attorney, Agent, or Firm—Sprung, Felfe, Horn, Lynch & Kramer

[57] ABSTRACT

An artificial heart valve consists basically of a valve ring and a valve flap in the form of a disc which is pivotally mounted eccentrically in the valve ring, the external circumferential surface of the valve flap cooperating with the internal contour of the valve ring to form a sealing line extending round the circumference of the valve flap. Manufacture of the heart valve can be substantially simplified if the valve ring is obtained by a slightly oblique cut through a hollow cylinder and the valve flap by an oblique cut made at a slightly larger angle through a solid circular cylinder which constitutes the core of the hollow cylinder.

6 Claims, 6 Drawing Figures

ARTIFICIAL HEART VALVE

This invention relates to an artificial heart valve comprising a valve ring and a valve flap in the form of a disc which is pivotally mounted eccentrically in the valve ring and the external circumferential surface of which cooperates with the internal contour of the valve ring to form a sealing surface extending round the circumference of the valve flap.

Artificial heart valves have become increasingly important in heart surgery in recent years. Various models are already on the market (see, for example, Trade Catalogue of Bjork-Shiley Laboratories, Inc. P.O. Box 11707, Santa Ana, Calif. 92711). These heart valves must satisfy stringent biophysical requirements. The most important problems are those of haemolysis and biocompatibility. Reference may be made in this connection to the work by C. J. Knight and D. M. Taylor, University of Edinburgh, in particular British Patent Specification No. 1,327,371 and C. J. Knight, Ph.D. Thesis, University of Edinburgh, 1973.

These documents explain among other things the geometrical conditions necessary for obtaining a sealing surface extending around the circumference of the valve flap. It is stated that the surface of the valve ring on which the seal is formed must taper in cross-section so that it has a frusto-conical form widening out in the direction of the blood flow. The valve flap is mounted eccentrically in this cross-section. In plan view, the valve flap has the form of an ellipse. The flap may be constructed as a disc or it may be profiled in the form of an air foil. It is mounted by means of grub screws which are screwed through the valve ring into the valve flap in the direction of the axis of rotation.

Clear geometrical arguments are given to show that the desired sealing effect can only be obtained if the valve ring is conical. A sketch is provided to illustrate that a valve flap which is elliptical in plan view can rotate inside a cylindrical valve ring only if the axis of rotation coincides with the short half axis. This in fact is true only in valve rings which are very large in the direction of flow, but it is precisely valve rings of this kind which should be avoided in artificial heart valves for medical reasons.

One important disadvantage of the heart valve described in these publications is that the valve flap is not obtained from a cylinder but by an oblique section through a cone. This complicates the manufacture of the valve. The same applies to the valve ring. Moreover, in the valve ring, mechanical working of the sealing surface is made very difficult by the need for conicity.

The heart valve of Bjork-Shiley is based on similar principles to those applied in the heart valve described above. In Bjork-Shiley's heart valve, a valve flap in the form of a circular disc is inserted in a valve ring which has a circular cross-section of opening. To prevent jamming of the circular disc inside the circular opening of the valve ring, a gap must be left between the valve ring and the external diameter of the disc. This gap has a serious disadvantage in that it can cause blood damage due to the flow conditions.

It is an object of the present invention to obviate the above mentioned disadvantages of the known artificial heart valves. In particular, the basic geometric concept of the heart valve should be such that very simple manufacture can be achieved without entailing the risk of haemolytic complications.

According to the invention, there is provided an artificial heart valve comprising a valve ring and a valve flap which is pivotally mounted eccentrically in the valve ring and the circumferential surface of which cooperates with the internal contour of the valve ring to form a sealing line on the circumference of the valve flap, wherein the valve ring is obtained by making an oblique cut at a slight angle $\alpha_v$ through a hollow cylinder and the valve flap is obtained by making an oblique cut at a slightly greater angle $\alpha_s$ through a cylinder of circular cross-section which forms the core of the hollow cylinder.

This means that the external surface of the valve flap is cut out of the same cylinder of circular cross-section as that whose surface forms the internal surface of the valve ring but the angle between the axis of the cylinder and the perpendicular to the mid-plane of the valve flap is slightly greater than the angle between the aforesaid cylinder axis and the perpendicular to the end face of the valve ring. In this design a seal is formed along a line on the valve flap and on the internal contour of the valve ring and the cross-section of the valve flap are approximately circular.

According to a preferred feature of the invention, the angular difference $(\alpha_s - \alpha_v)$ between the two oblique sections is made as small as possible, the lower limit being that angle at which a tendency to jamming (self blocking) first appears in the valve flap. This self blocking and hence the angular difference $(\alpha_s - \alpha_v)$ depend on the material used. In practice, both $\alpha_s$ and $(\alpha_s - \alpha_v)$ amount to only a few degrees (maximum 10°). The optimum values can easily be determined empirically.

The axis of rotation of the valve flap preferably lies nearer to the opening side of the flap than that plane in the flap which is defined by the sealing line. The means of mounting the flap advantageously consists of a half open swivel joint on the opening side whereas on the closing side a support with pins or stirrups is provided in such a manner as to prevent displacement of the flap towards the closing side and at the same time to provide an abutment for the flap when open.

According to another feature of the invention, the edges extending round the circumference of the flap are rounded off so that the sealing surface on the valve flap is restricted to a narrow strip. This arrangement improves the fluid flow properties. Another fluid flow improvement is obtained by giving the flap the form of an aero foil in profile so that the blood flow inside the ventricle assists the closing movement of the valve flap towards the end of the diastolic or filling phase of the heart.

The advantages of Bjork-Shiley's heart valve are fully realized in the heart valve according to the invention without the disadvantage of the circumferential leakage gap. Although Taylor's heart valve avoids this gap, it does so only at the expense of a very complicated method of manufacture. The heart valve according to the invention succeeds in realizing the advantages of the known artificial heart valves without the disadvantages mentioned above. In particular, in the heart valve according to the invention, a completely reliable seal is obtained over an area in the form of a strip and yet when the flap opens the full cross-section of the valve is released. It is particularly advantageous in this connection that the sealing surfaces are sections of cylindrical surfaces of circular cross-section which, as is well known, can be easily and inexpensively produced even when close tolerances are required. This enables the artificial heart valve to be manufactured from materials which, although extremely suitable from a biological point of view, are mechanically very difficult to process. Another advantage is that the seal is obtained in the form of an exact strip without risk of jamming of the flap in the valve ring (self blocking). Lastly, the design according to the invention makes it possible to use a form of flap which has such suitable flow technical properties that the forces of flow acting on the flap during the diastolic or filling phase of the heart already initiate a closing movement towards the end of this phase. This is extremely important for eliminating the back flow from the ventricle to the auricle as far as possible. Moreover, the oblique position of the closing plane of the valve in relation to the circular cylinder whose circumferential surface forms the internal surface of the valve ring ensures that the valve flap will not hit hard against the sealing surface as is the case in the usual artificial heart valves, in which the flap executes a sudden, jerky movement. The heart valve according to the invention is therefore also particularly advantageous from a haemolytic point of view.

An embodiment of the invention will now be described below with reference to the accompanying drawings in which.

Figure 1:
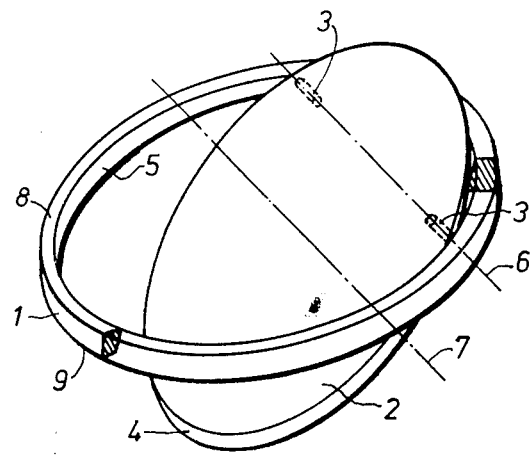
FIG. 1 is a view in perspective of a heart valve according to the invention.

The artificial heart valve shown in FIG. 1 consists of a valve ring 1, a valve flap 2 and joints 3 for mounting the flap 2 on the ring 1. The joints 3 are inserted partly in the valve ring 1 and partly in the valve flap 2. The valve ring 1 may be made of plastics or a suitable metal, e.g. titanium. It is bound by a circular seam of a textile thread in the usual manner (not shown). The internal contour of the valve ring 1 and hence the sealing surface 5 has been cut out of the surface of a circular cylinder by sections through two parallel planes 8 and 9 which also form the end faces of the ring 1, the axis of said cylinder being tilted clockwise from the mid-line 7 by a small angle $\alpha_v$.

The valve flap 2 is substantially in the form of a disc and may be made of plastics, metal or carbon. The external surface 4 of the valve flap 2 is cut out of the same circular cylinder as that whose surface forms the internal surface 5 of the valve ring. In the case of the flap 2, however, the angle of inclination $\alpha_s$ of the axis of the cylinder in relation to the perpendicular on the mid-plane of the valve flap is slightly greater than the angle $\alpha_v$ between the aforesaid cylinder axis and the perpendicular on the end face 8 of the valve ring. Depending on the material or the combination of materials used for the valve flap and valve ring, the angle of inclination $\alpha_v$ of the axis of the circular cylinder from which the surface 5 and surface 4 have been cut out is suitably chosen in relation to the plane 8 and the mid-plane of the flap 2 so that no self-blocking or jamming occurs when the valve is closed, that is to say when there is linear contact (along the sealing line) between the surfaces 5 and 4.

Figure 2:
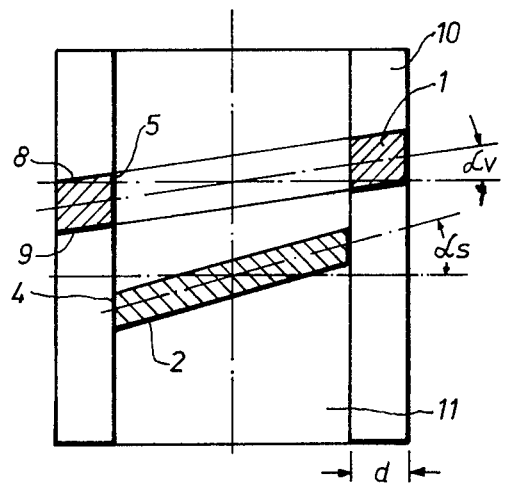
FIG. 2 illustrates the geometrical relationship between the valve ring and the valve flap.

The three-dimensional geometric relation between valve ring 1 and valve flap 2 described above is illustrated in FIG. 2. The valve ring 1 is obtained by an oblique section (angle $\alpha_v$) through a hollow cylinder 10 of circular cross-section which has a wall thickness d. The valve flap 2 is obtained by an oblique section (angle $\alpha_s$) through the core 11 of the hollow cylinder 10. The difference between the angle of inclination of the cuts made for obtaining valve ring 1 and the angle of inclination of the cuts made for obtaining the flap 2 is $\alpha_s - \alpha_v$. It is important that the external surface 4 of the valve flap 2 conforms to the internal surface 5 of the valve ring 1 since both surfaces 4 and 5 belong to the same circular cylinder 11.

Figure 3:
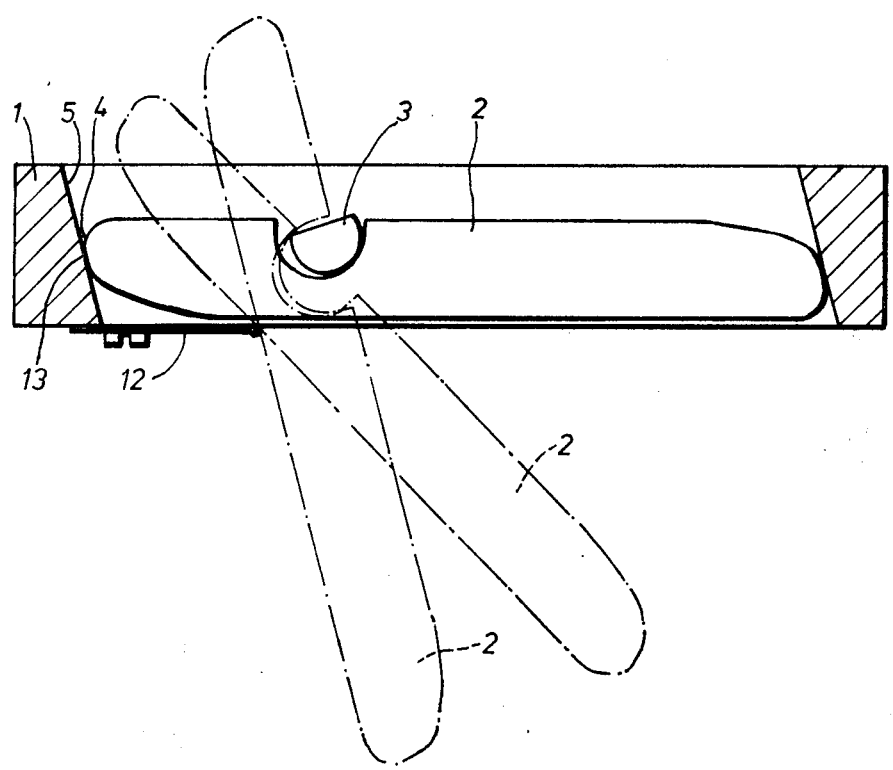
FIG. 3 is a cross-section through the valve, showing various positions of the valve flap.

Various positions of the valve flap 2 and its mounting are shown in FIG. 3. It can be seen that the flap 2 is eccentrically mounted by means of the pins 3 inserted in the valve ring 1. The mounting is in the form of a half open swivel joint. The bracket 12 serves as abutment for the flap 2 when open. The basic principle of the seal can be seen when the valve is closed. Owing to the difference between angle $\alpha_s$ and angle $\alpha_v$, a peripheral sectional line is obtained between the internal surface 5 of the valve ring and the external surfaces 4 of the valve flap 2. Since, however, angles $\alpha_s$ and $\alpha_v$ differ only slightly from each other, a sliding section is obtained, that is to say the section line (sealing line) 13 is extended into an annular sealing zone around the circumference of the valve flap. The size of this zone depends on the angles and on the properties of the material such as deformability.

As shown in FIG. 3, the edges on the circumference of the flap 2 are rounded off. This is advantageous from a fluid flow point of view.

Figure 4A:
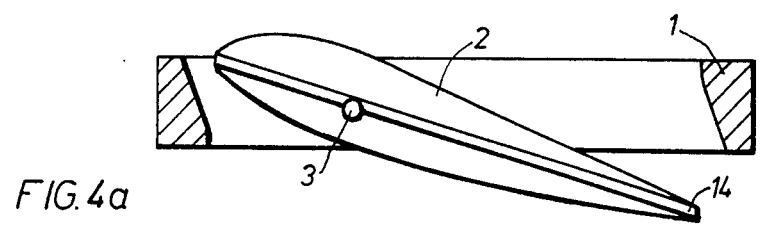
FIGS. 4a–4c show various possible arrangements for mounting the valve flap.
Figure 4B:
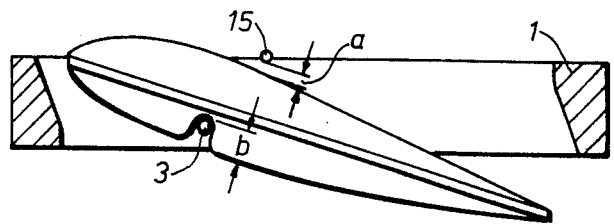
Figure 4C:
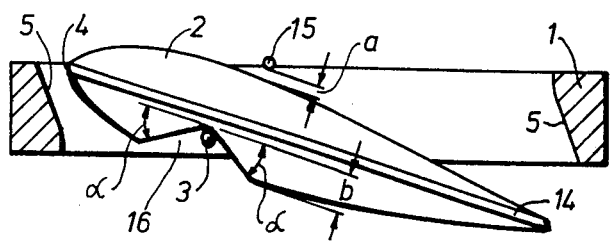

Various possible methods of mounting the flap 2 are illustrated in FIGS. 4a to 4c. The figures also show the profile of the flap 2 in the form of an aero foil. The pin bearing in FIG. 4a corresponds to that of FIG. 1. The bearings may be in the form of simple cylindrical pins inserted through the valve ring 1 into the valve flap 2. The axis 6 of the joint extends parallel to the minor 7 of the cross-section of the valve ring. The axis of rotation does not lie in the plane 14 defined by the sealing zone but is shifted towards the opening side of the valve. The half open swivel bearing shown in FIG. 4b is similar to the bearing of FIG. 3. On the closing side, a pin 15 is in this case inserted in the valve ring 1. This pin prevents displacement of the flap towards the closing side and at the same time serves as an abutment for the valve flap when open. The pins 3 and 15, must be so arranged that $a < b$ in every position of the valve flap.

FIG. 4c illustrates a special case of a half open swivel joint. The joint pin 3 is in this case seated in a relatively shallow recess 16 worked into the opening side of the valve flap 2. This arrangement is particularly suitable from a fluid flow point of view. An abutment pin 15 is again provided on the other side. By analogy with the design shown in FIG. 4b, the rule applies to the position of the pins 3 and 15 that $a$ must be less than $b$. The angle $\alpha$ which defines the steepness of the side of the recess 16 must not be less than a certain critical angle $\alpha_{cr}$. Self blocking occurs when $\alpha = \alpha_{cr}$. $\alpha_{cr}$ depends on the geometry of the circumferential surface 4 of the valve flap and the internal surface 5 of the valve ring as well as on the nature of the materials used and it must be determined empirically.

What we claim is:

1. An artificial heart valve comprising a valve ring obtained by making an oblique cut at an angle $\alpha_v$ no greater than 10° through a hollow cylinder and a valve flap obtained by making an oblique cut at an angle $\alpha_v$ slightly greater than $\alpha_v$, through a cylinder of circular cross-section which forms the core of the hollow cylinder and means pivotally mounting the valve flap eccentrically in the valve ring for movement between an open position and a closed position wherein the circumferential surface thereof cooperates with the internal contour of the valve ring to form a sealing line around the circumference of the valve flap.

2. An artificial heart valve according to claim 1, wherein the difference between the angles of the two oblique cuts ($\alpha_s - \alpha_v$) is as small as possible and greater than that angle at which the valve body begins to show a tendency to jam and thus self-block.

3. An artificial heart valve according to claim 1, wherein the axis of rotation of the valve flap is nearer to the opening side of the valve ring than the plane defined by the sealing line within the valve flap.

4. An artificial heart valve according to claim 3, wherein the means mounting the valve flap comprises a half open swivel joint towards the opening side and a support provided on the closing side to prevent the displacement of the valve flap towards the closing side and at the same time abut against the valve flap when in the open position.

5. An artificial heart valve according to claim 1 wherein the circumferential edges of the valve flap are rounded off.

6. An artificial heart valve according to claim 1 wherein the valve flap has an aerofoil profile, whereby, in use, the blood flow inside the ventricle assists the closing movement of the valve flap towards the end of the filling phase of the heart.

* * * * *